United States Patent [19]

Clifford

[11] 4,388,251
[45] Jun. 14, 1983

[54] METHOD FOR PREPARING 2-CHLOROBENZOYL CHLORIDE

[75] Inventor: David P. Clifford, King's Lynn, England

[73] Assignee: The Dow Chemical Company Limited, King's Lynn, England

[21] Appl. No.: 343,645

[22] Filed: Jan. 28, 1982

Related U.S. Application Data

[63] Continuation of Ser. No. 202,914, Nov. 3, 1980, abandoned.

[51] Int. Cl.$^3$ ............................................. C07C 51/58
[52] U.S. Cl. ................................. 260/544 D; 260/694
[58] Field of Search ..................................... 260/544 D

[56] References Cited

U.S. PATENT DOCUMENTS

| | | |
|---|---|---|
| 1,851,832 | 3/1932 | Henderson et al. |
| 2,806,061 | 9/1957 | Wygant |
| 3,274,242 | 9/1966 | Etherington et al. |
| 3,996,274 | 12/1976 | Jurewicz |
| 4,175,095 | 11/1979 | Maahs et al. ..................... 260/544 Y |

OTHER PUBLICATIONS

"Organic Synthesis" Coll. vol. I (1932), pp. 148–149, John Wiley, Publ.
Kirk–Othmer, "Encyclopedia of Chemical Technology", 2nd Ed. vol. 1, (1963), p. 223, Interscience Publ.

*Primary Examiner*—Natalie Trousof
*Assistant Examiner*—L. Hendriksen
*Attorney, Agent, or Firm*—S. Preston Jones; Ronald G. Brookens

[57] ABSTRACT

The present application is directed to the preparation of 2-chlorobenzoyl chloride by the reaction of 2-chlorobenzaldehyde with chlorine in the presence of phosphorus pentachloride.

3 Claims, No Drawings

METHOD FOR PREPARING 2-CHLOROBENZOYL CHLORIDE

CROSS-REFERENCE TO RELATED APPLICATION

This is a continuation of application Ser. No. 202,914, filed Nov. 3, 1980, now abandoned.

BACKGROUND OF THE INVENTION

The chlorination of 2-chlorobenzaldehyde to provide 2-chlorobenzoyl chloride is known. See, for example, Chemical Abstracts Vol. 23, 2164. The temperatures employed were 150° to 160° C. for a time of 15 hours. The yield was 81%.

SUMMARY OF THE INVENTION

This invention relates to a method for preparing 2-chlorobenzoyl chloride and more particularly relates to a method for chlorinating 2-chlorobenzaldehyde to provide 2-chlorobenzoyl chloride in high yield and purity.

It has now been found that the time of the chlorination reaction may be considerably reduced and the desired 2-chlorobenzoyl chloride obtained in yields of over 90% with purities above 95% by utilizing a catalytic amount of phosphorus pentachloride in the reaction.

The reaction may be carried out at a temperature of from 50° to 200° C., but is preferably conducted at 140° to 170° C., with or without the presence of an inert solvent. At lower temperatures, somewhat longer reaction times are necessary than at higher temperatures, as is readily understood by those skilled in the art.

The phosphorus pentachloride is employed in an amount such that the aldehyde to $PCl_5$ ratio is from 1:0.05 to 1:0.2, preferably 1:0.1 to 1:0.15.

The reaction is substantially complete in from 5 to 8 hours.

The reaction is further illustrated by the following examples.

EXAMPLE 1

Phosphorus pentachloride (41.5 g, 0.2 mole) was added to 2-chlorobenzaldehyde (289.7 g, 2.0 mole, 97%). After the ensuing exotherm had subsided, the resulting red solution was heated to 160° C. A stream of chlorine was introduced through a sparge tube into the solution for a period of six hours. (Gas chromatography indicated 96.5% conversion.) The solution was then cooled and distilled under reduced pressure giving 325.4 grams of 2-chlorobenzoyl chloride which boiled at 135° to 140° C. at 16 millimeters of mercury. The yield of the desired product was 93% (98.5% pure).

EXAMPLE 2

Following the above procedure, except that the aldehyde to $PCl_5$ ratio was 1:0.15, the reaction time was 7.3 hours and the reaction temperature was 162° C., a conversion of 98.6% of the 2-chlorobenzaldehyde to the desired 2-chlorobenzoylchloride was obtained.

What I claim is:

1. A process for preparing 2-chlorobenzoyl chloride which comprises reacting 2-chlorobenzaldehyde with chlorine in the presence of phosphorus pentachloride at a temperature of from 50° to 200° C. and wherein the 2-chlorobenzaldehyde:phosphorus pentachloride ratio is from 1:0.05 to 1:0.2.

2. Process of claim 1 wherein the reaction temperature is from 140° to 170° C.

3. Process of claim 2 wherein the aldehyde:$PCl_5$ ratio is from 1:0.1 to 1:0.15.

* * * * *